(12) United States Patent
Chappuis

(10) Patent No.: US 8,900,236 B2
(45) Date of Patent: Dec. 2, 2014

(54) INTERNAL PEDICLE INSULATOR IMPLANTS ASSEMBLIES AND METHODS OF USE

(76) Inventor: James Chappuis, Marietta, GA (US)

( * ) Notice: Subject to any disclaimer, the term of this patent is extended or adjusted under 35 U.S.C. 154(b) by 1881 days.

(21) Appl. No.: 11/751,708

(22) Filed: May 22, 2007

(65) Prior Publication Data

US 2007/0219553 A1 Sep. 20, 2007

Related U.S. Application Data

(63) Continuation-in-part of application No. 11/712,257, filed on Feb. 28, 2007, which is a continuation-in-part of application No. 11/110,005, filed on Apr. 20, 2005.

(60) Provisional application No. 60/563,797, filed on Apr. 20, 2004.

(51) Int. Cl.
*A61B 17/56* (2006.01)
*A61B 17/68* (2006.01)
*A61B 17/70* (2006.01)
*A61F 2/46* (2006.01)

(52) U.S. Cl.
CPC ............ *A61B 17/686* (2013.01); *A61B 17/7001* (2013.01); *A61B 17/7098* (2013.01); *A61F 2002/4631* (2013.01)
USPC ...................................................... 606/86 R

(58) Field of Classification Search
USPC .......... 606/86 R, 304; 411/55, 59, 61–62, 73, 411/354, 452
See application file for complete search history.

(56) References Cited

U.S. PATENT DOCUMENTS

| | | | | | |
|---|---|---|---|---|---|
| 517,591 | A | * | 4/1894 | Robinson | 174/152 G |
| 1,835,243 | A | * | 12/1931 | Schaffert | 403/410 |
| 2,060,970 | A | * | 11/1936 | Belden | 16/404 |
| 2,499,315 | A | * | 2/1950 | Johnson | 411/360 |
| 3,197,243 | A | * | 7/1965 | Brenneke | 403/372 |
| 3,937,122 | A | * | 2/1976 | Riedel | 411/34 |
| 4,340,330 | A | * | 7/1982 | Reidel | 411/33 |
| 4,580,767 | A | * | 4/1986 | Zimmerman | 256/10 |
| 4,893,973 | A | * | 1/1990 | Herb | 411/55 |
| 5,431,660 | A | * | 7/1995 | Burke | 606/104 |
| D406,226 | S | * | 3/1999 | Larson | D8/354 |
| 6,093,207 | A | * | 7/2000 | Pisharodi | 623/17.16 |
| 6,214,012 | B1 | * | 4/2001 | Karpman et al. | 606/93 |
| D447,930 | S | * | 9/2001 | Larson | D8/354 |
| 6,306,156 | B1 | * | 10/2001 | Clark | 606/216 |
| 6,765,148 | B2 | * | 7/2004 | Rix | 174/650 |
| 7,083,621 | B2 | * | 8/2006 | Shaolian et al. | 606/86 A |
| 7,686,555 | B1 | * | 3/2010 | Larson et al. | 411/367 |
| 2004/0267277 | A1 | * | 12/2004 | Zannis et al. | 606/99 |
| 2006/0235410 | A1 | * | 10/2006 | Ralph et al. | 606/72 |

* cited by examiner

*Primary Examiner* — Christian Sevilla
(74) *Attorney, Agent, or Firm* — McHale & Slavin, P.A.

(57) ABSTRACT

Internal pedicle insulator implants, assemblies and related methods are provided. A representative method includes: placing an implant at least partially about an intermediate portion of the fixture, the implant having an inner surface; driving a distal end of the implant into tissue into which the fixture is inserted; and dispensing cement such that the cement is located between the inner surface of the implant and an exterior of the fixture.

10 Claims, 3 Drawing Sheets

(A-A)

(B-B)

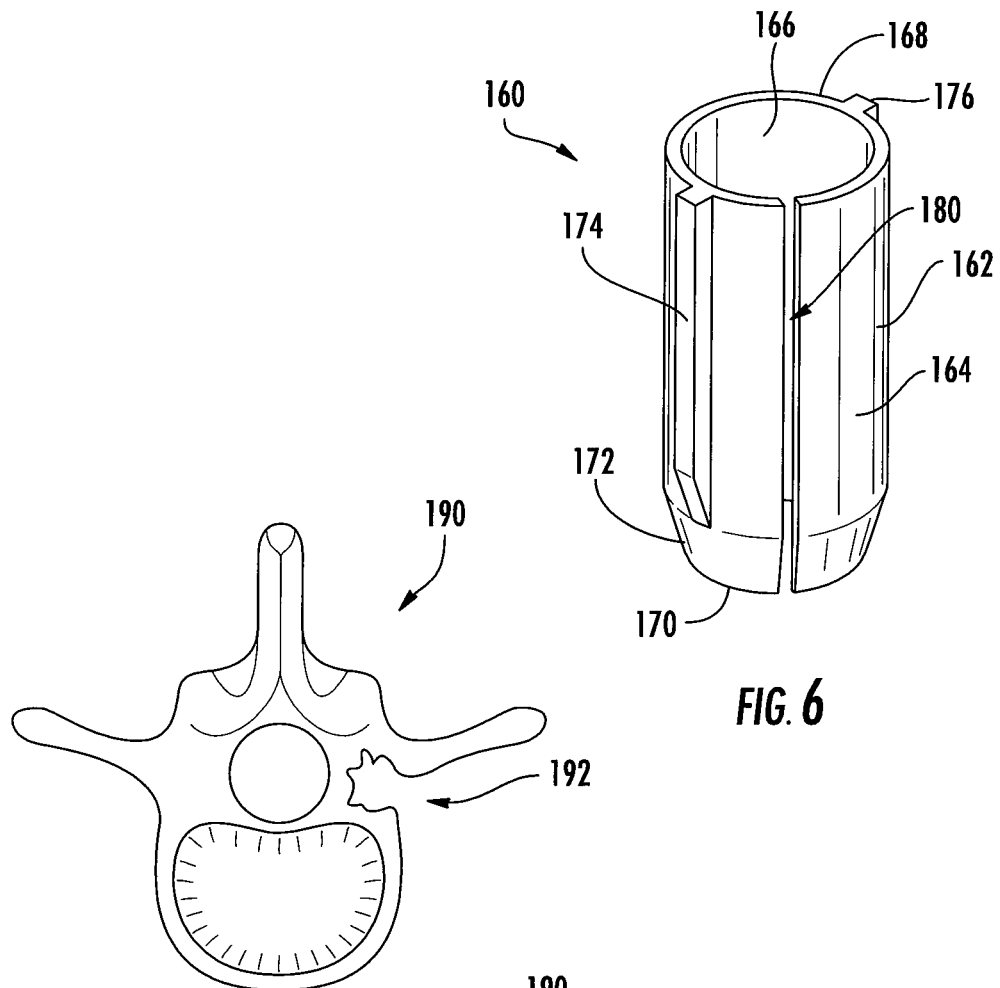
FIG. 6
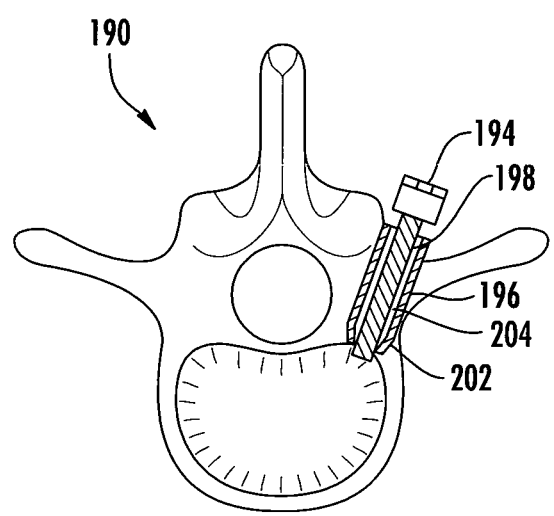
FIG. 7
FIG. 8

INTERNAL PEDICLE INSULATOR IMPLANTS ASSEMBLIES AND METHODS OF USE

CROSS-REFERENCE TO RELATED APPLICATIONS

This application is a Continuation-in-Part application, which claims priority to U.S. Patent application entitled, "Internal Pedicle Insulator Apparatus and Method of Use," having Ser. No. 11/712,257, filed on Feb. 28, 2007, which claims priority to U.S. Patent application entitled, "Internal Pedicle Insulator Apparatus and Method of Use," having Ser. No. 11/110,005, filed on Apr. 20, 2005, which claims priority to U.S. provisional application entitled, "Internal Pedicle Insulator Apparatus" having Ser. No. 60/563,797, filed on Apr. 20, 2004, each of which is entirely incorporated herein by reference.

TECHNICAL FIELD

The present invention generally relates to surgical instruments and tools, and in particular, relates to an internal pedicle insulator apparatus.

DESCRIPTION OF THE RELATED ART

The human spine is composed of a column of thirty-three bones, called vertebra, and their adjoining structures. The twenty-four vertebrae nearest the head are separate bones capable of individual movement and are generally connected by anterior and posterior longitudinal ligaments and by discs of fibrocartilage, called intervetebral discs, positioned between opposing faces of adjacent vertebrae. The twenty-four vertebrae are commonly referenced in three sections. The cervical spine, closest to the head and often referenced as the "neck," comprises the first seven vertebrae of the spine. The thoracic spine and the lumbar spine are below the cervical spine. Each of the vertebra include a vertebral body and a dorsal arch, which enclose an opening, called the vertebral foramen, through which the spinal cord and the spinal nerve pass. The remaining nine vertebrae below the lumbar spine are fused to form the sacrum and the coccyx and are incapable of individual movement.

The degeneration of any portion of the lumbar spine can result in instability of the spine, which can lead to impingement or damage to the spinal cord or nerve roots. Impingement of the spinal column or nerve root can result in pain. Damage to spinal cord or nerve roots can result in reduced motor skills or even paralysis. Degeneration of the lumbar spine can be a result of fractures, tumors or other various degenerative diseases.

It is well known that utilization of pedicle screws for posterior lumbar stabilization procedures. These procedures typically include inserting a pedicle screw posteriorly into the pedicle or pillar of the lumbar spine. The screw is then connected to plates or rods for stabilization of the lumbar spine. A bone graft also can be added to help solidify the stabilization. The pedicle screw may be inserted off center, such as, for example, too medial, which may impinge on the associated nerve root causing pain. This requires a repositioning of the screw. However, even after repositioning there may be an effect on the pedicle wall, which can still cause nerve root irritation. Such procedures are also susceptible to loosening of the screw.

SUMMARY

Internal pedicle insulator implants, assemblies and related methods are provided. In this regard, an exemplary embodiment of an internal pedicle insulator implant comprises: a cylindrical wall having a first end and a second end, the second end exhibiting an annular taper; a slot extending between the first end and the second end such that, when viewed in plan view, the implant is generally C-shaped; and a first fin extending outwardly from an outer surface of the wall, the fin being operative to reduce a tendency of the implant to rotate after insertion into tissue An exemplary embodiment of an implant assembly comprises: an implant having a wall defining an interior cavity and having a first end and a second end, and a first fin extending outwardly from an outer surface of the wall, the fin being operative to reduce a tendency of the implant to rotate after insertion into tissue.

An embodiment of a method for stabilizing a surgical fixture comprises: placing an implant at least partially about an intermediate portion of the fixture, the implant having an inner surface; driving a distal end of the implant into tissue into which the fixture is inserted; and dispensing cement such that the cement is located between the inner surface of the implant and an exterior of the fixture.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 6 is a schematic diagram depicting another embodiment of an implant.

FIG. 7 is a schematic diagram depicting a degraded vertebral body.

FIG. 8 is a schematic diagram depicting the vertebral body of FIG. 7 with an embodiment of an implant and pedicle screw fixed therein.

DETAILED DESCRIPTION

Figure 1:
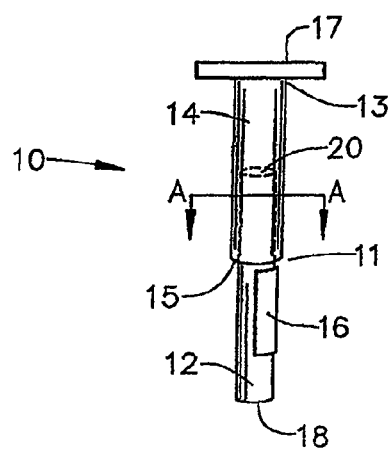
FIG. 1 is a side view of an embodiment of the internal pedicle insulator apparatus of the present invention.

FIG. 1 illustrates one preferred embodiment of an internal pedicle insulator apparatus 10. The internal pedicle insulator apparatus 10 comprises an inner insertion rod 12, an outer insertion rod 14, and an internal pedicle insulator implant 16.

The inner insertion rod 12 has a bottom end 18 and an opposing top end 20. It is preferable that the inner insertion rod 12 has a substantially round cross-section. However, it should be noted that the inner insertion rod 12 can comprise any suitable configuration. The inner insertion rod 12 can comprise any suitable material, such as titanium, as merely one example.

The outer insertion rod 14 has a lower end 11 and an opposing upper end 13. An opening 15 is disposed at the lower end 11. An optional handle 17 can be disposed toward the upper end 13 of the outer insertion rod 14 to facilitate use of the internal pedicle insulator apparatus 10. An opening at the upper end 13 of the outer insertion rod 14 through which the inner insertion rod 12 can pass can also be included (not shown). It is preferable that the outer insertion rod 14 has a substantially round cross-section. It should be noted, however, that the outer insertion rod 14 can comprise any suitable cross-section. The outer insertion rod 14 can comprise titanium, however, it should be understood that the outer insertion rod 14 can comprise any suitable material.

The outer insertion rod 14 is arranged and configured to receive the inner insertion rod 12 through the opening 15 disposed at the lower end 11 of the outer insertion rod 14. The inner insertion rod 12 is preferably slidably inserted into the outer insertion rod 14 such that the upper end 13 of the outer insertion rod 12 substantially corresponds to the top end 20 of the inner insertion rod 12. Similarly, the lower end 11 of the outer insertion rod 14 substantially corresponds with the bottom end 18 of the inner insertion rod 12. The inner insertion rod 12 is laterally slidable within the outer insertion rod 14.

Figure 1A:
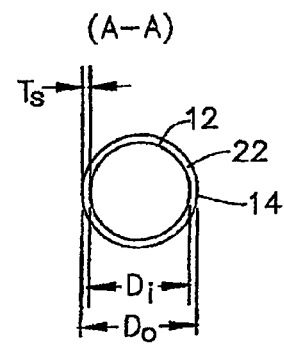
FIG. 1A is a cross-sectional top view of an embodiment of the internal pedicle insulator apparatus illustrated in FIG. 1.

Referring next to FIG. 1A, in one embodiment it is preferable that the outer insertion rod 14 is defined by a diameter $D_o$. The inner insertion rod 12 is defined by a diameter $D_i$. It is preferable that $D_o$ is greater than $D_i$ to facilitate the inner insertion rod 12 being slidably disposed within the outer insertion rod 14. It is further preferable that $D_o$ is less than $D_i$ such as to leave a space 22 having a thickness $T_s$ when the inner insertion rod 16 is disposed within the outer insertion rod 14.

Figure 1B:
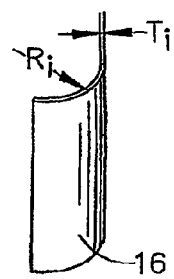
FIG. 1B is a perspective view of an embodiment of an internal pedicle insulator implant of the internal pedicle insulator apparatus illustrated in FIG. 1.

As shown in FIG. 1B, in one embodiment the internal pedicle insulator implant 16 is substantially rectangular in shape and curved. It should be understood, however, that the internal pedicle insulator implant 16 can comprise any suitable shape and configuration. In this embodiment it is preferable that the internal pedicle insulator implant 16 is curved as defined by a radius $R_i$. It is preferable that the radius $R_i$ of the internal pedicle insulator implant 16 substantially corresponds to a pedicle screw 104 with which the internal pedicle insulator implant 16 is to be used. The internal pedicle insulator implant 16 is also defined by a thickness $T_i$. It is preferable that the thickness $T_i$ is greater than the thickness $T_s$ of space 22. The internal pedicle insulator implant 16 preferably comprises Poly Ether Ether-Ketone, but can comprise any suitable material.

Figure 2:
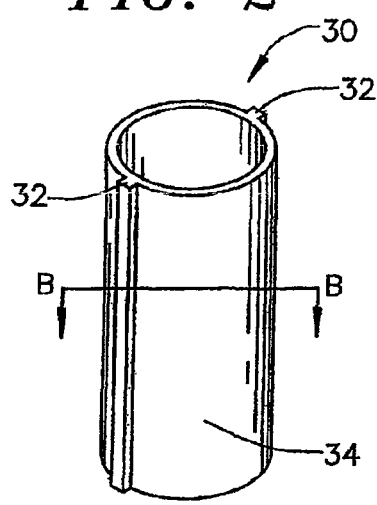
FIG. 2 is a perspective view of an embodiment of an internal pedicle insulator implant of the internal pedicle insulator apparatus illustrated in FIG. 1.
Figure 2A:
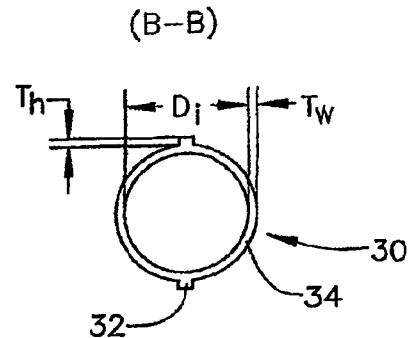
FIG. 2A is a cross-sectional top view of an embodiment of an internal pedicle insulator implant illustrated in FIG. 2.

FIGS. 2 and 2A illustrate another embodiment of an internal pedicle insulator implant 30. The internal pedicle insulator implant 30 is substantially tubular in shape and comprises a wall 34. The internal pedicle insulator implant 30 has a substantially circular cross-section, defined by a diameter $D_i$. The diameter $D_i$ is preferably arranged and configured to substantially correspond to a pedicle screw 104 with which the internal pedicle insulator implant 30 is to be used. Although a substantially circular cross-section is illustrated, it should be understood that the internal pedicle insulator can have any desired cross-sectional shape.

The internal pedicle insulator 30 optionally comprises at least one anti-rotation fin 32 extending outward from the wall 34. The anti-rotation fins 32 can extend the length of the wall 34 of internal pedicle insulator 30 or only a portion of the length. The anti-rotation fins 32 can comprise any configuration that discourage rotation of the internal pedicle insulator 30 when disposed in a desired position. In one embodiment, a thickness $T_w$ of the wall 34 of the internal pedicle insulator implant 30 in addition to a height $T_h$ of an anti-rotation fin 32 extending from the wall 34 is greater than thickness $T_s$ of the space 22 between the inner insertion rod 12 and the outer rotation rod 14 when the inner insertion rod 12 is disposed within the outer rotation rod 14.

In another embodiment the internal pedicle insulator implant 30 includes no anti-rotation fin 32 (not shown). In this embodiment, it is preferable that a thickness $T_w$ of a wall of the internal pedicle insulator implant 30 is greater than the thickness $T_s$ of the space 22 formed by the inner insertion rod 12 and the outer insertion rod 14 when the inner insertion rod 12 is disposed inside the outer insertion rod 14.

Figure 3:
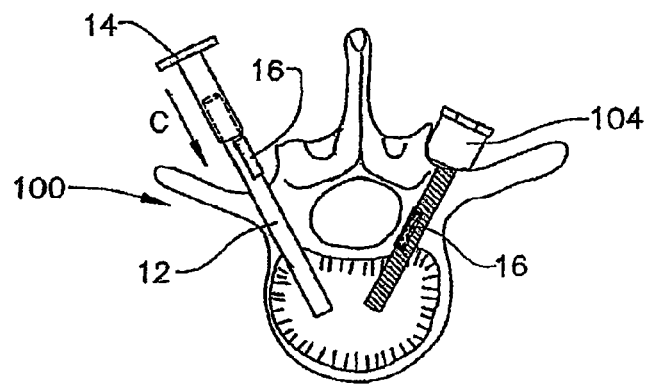
FIG. 3 is a side view of the internal pedicle insulator apparatus illustrated in FIG. 1 in use.

FIG. 3 illustrates the internal pedicle insulator apparatus 10 in use. A pedicle screw with which the internal pedicle insulator implant 16 is to be used is first removed from its position within the vertebral body. The inner insertion rod 12 is positioned as desired in the vertebral body 100, such as in a channel created by the pedicle screw 104. The internal pedicle insulator implant 16 is positioned adjacent the inner insertion rod 12. The outer insertion rod 14 is positioned around the inner insertion rod 12 via the opening 15 disposed at the lower end 11 of the outer insertion rod 14. The outer insertion rod 14 is moved in direction C toward the bottom end 18 of the inner insertion rod 12. As the outer insertion rod 14 is moved in direction C, the outer insertion rod 14 is moved toward the internal pedicle insulator implant 16 until the outer insertion rod 14 engages the internal pedicle insulator 16. Pressure is applied to the outer insertion rod 14 in direction C to slide the internal pedicle insulator 16 along the inner insertion rod 12 toward the vertebral body 100 until the internal pedicle insulator 16 is appropriately positioned within the vertebral body 100. The internal pedicle insulator implant 16 is held in position by friction applied to its curved configuration when properly inserted into position. After the internal pedicle insulator implant 16 is disposed in a desired position, the pedicle screw 104 is returned to its position within the vertebral body.

Figure 4:
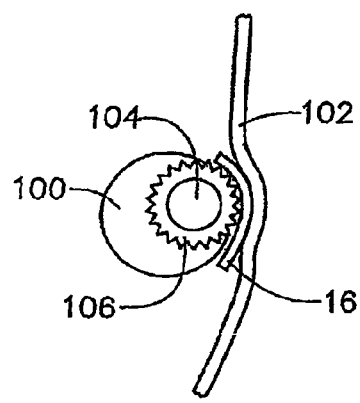
FIG. 4 is a top view of the internal pedicle insulator implant of the internal pedicle insulator apparatus illustrated in FIG. 1 in use.

FIG. 4 illustrates one embodiment of an internal pedicle insulator implant 16 in a desired position. As shown, the internal pedicle insulator implant 16 is positioned between an affected nerve root 102 and a jagged hole 106 in the vertebral body 100 resulting from a compromised pedicle screw 104.

Figure 5:
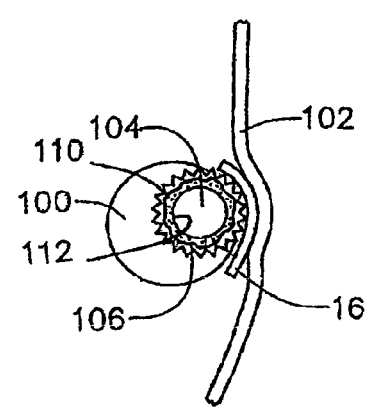
FIG. 5 is a top view of another embodiment of an internal pedicle insulator implant of the internal pedicle insulator apparatus in use.

FIG. 5 illustrates another embodiment of an internal pedicle insulator implant 16. In this example, however, the implant is located to prevent cement, e.g., PMMA, from contacting the nerve root 102. Notably, the cement 110 is provided to anchor the pedicle screw 104. In other embodiments, various other types of materials can be prevented from contacting a nerve by using an implant. Such a material can be an injectable biological substance, for example.

Although cement can be provided externally with respect to the screw, the embodiment of FIG. 5 involves a screw that incorporates holes or fenestrations e.g., fenestration 112. As such, the cement can be injected into the screw and then a portion of that cement can be pass through the fenestrations and into the surrounding tissue. Thus, the implant 16 serves as a physical barrier to prevent the cement from impinging upon the nerve root.

FIG. 6 schematically depicts another embodiment of an implant. In particular, implant 160 of FIG. 6 incorporates a wall 162. The wall is generally cylindrical in shape. The wall includes an outer surface 164, an inner surface 166, and opposing first and second ends 168, 170. Notably, the second end exhibits an annular taper 172 that can assist in driving of the implant into tissue.

The embodiment of FIG. 6 also incorporates fins 174, 176 that extend longitudinally along at least a portion of the length of the wall. Specifically, the fins extend from the first end and terminate at the annular taper. Although depicted with two opposing fins, other embodiments can incorporate various other numbers, sizes, shapes and locations of fins.

Note also that the embodiment of FIG. 6 includes a longitudinal slot 180. That is, although generally cylindrical, this embodiment of the implant does not exhibit a continuous annular surface. In operation, the slot enables the implant to be placed about a fixture, e.g., a screw, which is already mounted to tissue. That is, the slot enables the implant to be "snapped" around the screw by inserting the screw through the slot.

FIG. 7 depicts a vertebral body 190 that has a degraded pedicle 192. In FIG. 8, an implant assembly that includes a fixture 194, in this case a pedicle screw, is inserted into vertebral body 190 such that approximately a distal ⅓ of the screw is engaged within the tissue. Unfortunately, such a pedicle screw could exhibit toggle, which can degrade fixation of the screw within the tissue over time.

Also shown in FIG. 8 is an implant 196 of the implant assembly that is positioned about an intermediate portion of the screw. That is, the implant is positioned such that a portion of the screw is located in a cavity 198 defined by the inner surface of the implant.

The implant 196 is driven such that the second (in some embodiments, tapered) end 202 of the implant becomes anchored with the tissue into which the pedicle screw also is mounted. In this embodiment, a material 204 (e.g., cement) is used to fill at least a portion of the cavity formed between the inner surface of the implant and the screw. For instance, when the fixture is a fenestrated pedicle screw, cement can be injected into the screw for filling the cavity. In this manner, the implant not only reduces toggle by limiting pivot of the proximal end of the screw, the implant serves as a shield for limiting the ability of the cement to impinge upon adjacent tissue, such as nerves.

It should also be noted that use of an implant also can improve the pullout strength of a screw. This increase in pullout strength can be promoted by improving the structural integrity of the structure supporting the screw and/or providing increased frictional engagement with the surrounding tissue.

It should be emphasized that the above-described embodiments of the present invention are merely possible examples of implementations set forth for a clear understanding of the principles of the invention. Many variations and modifications may be made to the above-described embodiments of the invention without departing substantially from the spirit and principles of the invention. All such modifications and variations are intended to be included herein with the scope of this disclosure and the present invention and protected by the following claims.

Therefore, having thus described the invention, at least the following is claimed:

1. A pedicle insulator implant, implantable into a vertebral body of a spine, comprising:
    an inner cylindrical wall having a first end wall and a second end wall, the second end exhibiting an annular taper, said cylindrical wall having an inwardly directed smooth and non threaded surface;
    an outer cylindrical wall having a first end wall and a second end wall, having an inwardly directed smooth and non threaded surface, dimensioned to allow slidable insertion of the inner cylindrical wall;
    a slot extending between the first end wall and the second end wall such that, when viewed in plan view, the pedicle insulator implant is generally C-shaped; said slot defined by a first side edge and a second side edge and
    a first fin extending outwardly from an outer surface of the wall, the fin being operative to reduce a tendency of the implant to rotate after insertion into tissue
    whereby said pedicle insulator implant shields a pedicle screw that is implanted into the vertebral body and reduces nerve root irritation and diminishes the loosening of the pedicle screw.

2. The pedicle insulator implant of claim 1, wherein the fin extends longitudinally along the wall from the first end.

3. The pedicle insulator implant of claim 2, wherein the fin terminates at the taper of the second end.

4. A pedicle insulator implant assembly implantable into a vertebral body of a spine wherein said pedicle insulator implant comprises:
    an inner wall defining an interior cavity and having a first end and a second end, said wall having an inwardly directed smooth and non threaded surface; and
    an outer wall defining an interior cavity and having a first end and a second end, said wall having an inwardly directed smooth and non threaded surface dimensioned to allow the inner wall to slidably fit into the outer wall;
    a first fin extending outwardly from an outer surface of the wall, the fin being operative to reduce a tendency of the pedicle insulator implant to rotate after insertion into tissue of the vertebral body; whereby said pedicle insulator implant reduces nerve root irritation and diminishes the loosening of a pedicle screw.

5. The pedicle insulator implant assembly of claim 4, wherein the pedicle insulator implant further comprises a longitudinal slot extending between the first end and the second end.

6. The pedicle insulator implant assembly of claim 4, wherein the pedicle insulator implant is cylindrical.

7. The pedicle insulator implant assembly of claim 4, wherein the distal end of the pedicle insulator implant is annularly tapered.

8. The pedicle insulator implant assembly of claim 4, further comprising a fixture sized and shaped to be inserted within a cavity defined by an inner surface of the pedicle insulator implant.

9. The pedicle insulator implant assembly of claim 8, further comprising cement positioned within the cavity, at least a portion of the cement being located between the inner surface of the pedicle implant and an exterior of the fixture.

10. The pedicle insulator implant assembly of claim 9, wherein the fixture is a pedicle screw.

* * * * *